US010657662B2

(12) United States Patent
Lal et al.

(10) Patent No.: US 10,657,662 B2
(45) Date of Patent: *May 19, 2020

(54) DISPLAY METHOD AND SYSTEM FOR ENABLING AN OPERATOR TO VISUALIZE AND CORRECT ALIGNMENT ERRORS IN IMAGED DATA SETS

(71) Applicant: D4D Technologies, LLC, Richardson, TX (US)

(72) Inventors: Rakesh M. Lal, Irving, TX (US); James D. Susinno, Dallas, TX (US)

(73) Assignee: D4D Technologies, LLC, Richardson, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/675,874

(22) Filed: Aug. 14, 2017

(65) Prior Publication Data

US 2018/0068455 A1 Mar. 8, 2018

Related U.S. Application Data

(63) Continuation of application No. 13/031,282, filed on Feb. 21, 2011, now Pat. No. 9,730,776.
(Continued)

(51) Int. Cl.
*A61B 6/00* (2006.01)
*A61B 6/14* (2006.01)
(Continued)

(52) U.S. Cl.
CPC .............. *G06T 7/33* (2017.01); *A61B 6/14* (2013.01); *A61B 6/463* (2013.01); *A61B 6/465* (2013.01);
(Continued)

(58) Field of Classification Search
CPC ....... G06T 15/08; G06T 11/001; G06T 15/04; G06T 15/80; G06T 2207/30028;
(Continued)

(56) References Cited

U.S. PATENT DOCUMENTS

2006/0142657 A1* 6/2006 Quaid ................ A61B 17/1764
600/424
2006/0193521 A1* 8/2006 England .................... G01S 7/51
382/190
(Continued)

*Primary Examiner* — Haixia Du
(74) *Attorney, Agent, or Firm* — David H. Judson

(57) ABSTRACT

A method to visualize and correct alignment errors between paired 2D and 3D data sets is described. In a representative embodiment, a display interface used for dental implant planning includes one or more display areas that enable the operator to visualize alignment errors between the paired 2D and 3D data sets. A first display area renders 3D cone beam data. A second display area renders one or more (and preferably three (3) mutually orthogonal views) slices of the cone beam data. A third display area displays a view of a 2D scanned surface map (obtained from an intra-oral scan, or the scan of a model). According to a first aspect, the view of the 2D scanned surface map in the third display area is "textured" by coloring the 2D surface model based on the intensity of each 3D pixel (or "voxel") that it intersects.

12 Claims, 4 Drawing Sheets

Related U.S. Application Data

(60) Provisional application No. 61/307,535, filed on Feb. 24, 2010.

(51) Int. Cl.
*A61C 9/00* (2006.01)
*G06T 7/33* (2017.01)
*A61C 13/00* (2006.01)
*G16H 20/40* (2018.01)

(52) U.S. Cl.
CPC ............ *A61B 6/466* (2013.01); *A61C 9/0053* (2013.01); *G16H 20/40* (2018.01)

(58) Field of Classification Search
CPC ..... G06T 15/00; G06T 2210/41; G06T 17/00; G06T 2200/04; G06T 2207/10081; G06T 2207/10088; A61B 6/466
See application file for complete search history.

(56) References Cited

U.S. PATENT DOCUMENTS

| | | | | |
|---|---|---|---|---|
| 2009/0103793 | A1* | 4/2009 | Borland | G06T 15/08 382/131 |
| 2009/0316966 | A1* | 12/2009 | Marshall | A61B 6/5217 382/128 |

* cited by examiner

DISPLAY METHOD AND SYSTEM FOR ENABLING AN OPERATOR TO VISUALIZE AND CORRECT ALIGNMENT ERRORS IN IMAGED DATA SETS

BACKGROUND OF THE INVENTION

Technical Field

This disclosure relates generally to computer-assisted techniques for creating dental restorations.

Brief Description of the Related Art

The art of fabricating custom-fit prosthetics in the dental field is well-known. Prosthetics are replacements for tooth or bone structure. They include restorations, replacements, inlays, onlays, veneers, full and partial crowns, bridges, implants, posts, and the like. Typically, a dentist prepares a tooth for a restoration by removing existing anatomy, which is then lost. The resultant prepared area (a "preparation") is then digitized (or, in the alternative, a dental impression is taken) for the purpose of constructing a restoration, appliance or substructure. The restoration itself may be constructed through a variety of techniques including manually constructing the restoration, using automated techniques based on computer algorithms, or a combination of manual and automated techniques.

Computer-assisted techniques have been developed to generate three-dimensional ("3D") visual images of physical objects, such as a dental preparation. In general, the 3D image may be generated by a computer that processes data representing the surfaces and contours of a physical object. The computer displays the 3D image on a screen or a computer monitor. The computer typically includes a graphical user interface (GUI). Data is generated by optically scanning the physical object and detecting or capturing the light reflected off of the object. Based on processing techniques, the shape, surfaces and/or contours of the object may be modeled by the computer. During the process of creating a tooth restoration model, one or more user interface tools may be provided to facilitate the design process. One known display technique uses a computer monitor that, under software control, displays a 3-dimensional representation of a tooth model.

It is also known in the art to use such computer-aided design systems to facilitate the production of a crown to be placed on a custom implant abutment. Because the implant abutment is custom designed (i.e., to fit the implant), the interior of the crown that attaches to the abutment also needs to be custom designed for the particular case. The usual process followed is for an implant to be inserted into the jawbone (or maxillary-upper arch) of a patient. An abutment (made, for example, from titanium or zirconia) is then screwed (or placed or cemented) onto the top of the implant and is then adjusted by the dentist using dental tools. At this point, the abutment may be digitized by a 3D scanner, and a crown model generated using CAD techniques, and finally a physical crown (or appliance) milled out of a dental material such as ceramic, composite or metal. The abutment is scanned at the time it is customized (placed), i.e., at the time that the implant is first inserted. When customization of the implant is completed, either the abutment is removed for scanning outside the mouth, or the abutment is scanned inside the mouth while attached to the implant. U.S. Publication No. 20090087817, assigned to D4D Technologies, LLC, describes this approach.

Helical (or spiral) cone beam computed tomography (CBCT) is a known technique for three-dimensional (3D) computer tomography in which a source (typically X-rays) describes a helical trajectory relative to an object being scanned while a two-dimensional (2D) array of detectors measures the transmitted radiation on part of a cone of rays emanating from the source. Cone beam 3-D dental imaging systems provide dentists and specialists with high-resolution volumetric images of a patient's mouth, face and jaw areas. Three-dimensional views of all oral and maxillofacial structures allows for more thorough analysis of bone structures and tooth orientation to optimize implant treatment and placement, selection of the most suitable implant type and angulations prior to surgery. Representative commercial systems implementing these technologies are the i-CAT from Imaging Sciences International, Inc. and the GXCB-500 (powered by i-CAT) from Gendex Dental Systems, Inc.

Thus, it is well-known to use different imaging modalities (e.g., CT, MRI, OCT, ultrasound, microscopy, camera-based, etc.) to produce images for dental CAD CAM systems. In one use case, such as the planning for implant surgery, a first modality may be used to produce a scanned surface map of a patient's existing dentition, and a second modality may be used to produce 3D cone beam computed tomography data. Of course, each of the data sets provides different information, and it is desirable to provide a mechanism to align such data. While there are known techniques for this purpose, such techniques often produce less than optimal results. Errors in alignment may manifest themselves as distortions in an end result. For example, an alignment error between the 2D surface map and the 3D computed tomography data may result in inaccurate positioning of a dental implant device with respect to landmarks in either or both data sets. Moreover, because the data sets typically are acquired from significantly different imaging modalities, the characteristics of the data may be quite different, which exacerbates the problem for an automated solution. Due to these issues, most automated and semi-automated approaches to align such data sets may yield significant alignment errors. As a result, there is a need to provide a robust mechanism to allow users to visualize alignment errors, and to manually or automatically correct them.

BRIEF SUMMARY

A method to visualize and correct alignment errors between paired 2D and 3D data sets is described. In a representative embodiment, a display interface includes one or more display areas that enable the operator to visualize alignment errors between the paired 2D and 3D data sets. A first display area renders 3D cone beam data. A second display area renders one or more (and preferably three (3) mutually orthogonal views) slices of the cone beam data. A third display area displays a view of a 2D scanned surface map (obtained from an intra-oral scan, or the scan of a model). According to a first aspect of this disclosure, the view of the 2D scanned surface map in the third display area is "textured" by coloring the 2D surface model based on the intensity of each 3D pixel (or "voxel") that it intersects.

Although not meant to limit this disclosure, the visualization technique described above may be implemented within a dental implant planning software system used to plan and design an implant abutment to support a restoration.

BRIEF DESCRIPTION OF THE DRAWINGS

The subject matter herein may be better understood with reference to the following drawings and its accompanying description. Unless otherwise stated, the components in the figures are not necessarily to scale, emphasis instead being placed upon illustrating the principles of the invention. Moreover, in the figures, like referenced numerals designate corresponding parts throughout the different views.

DETAILED DESCRIPTION

Figure 1:
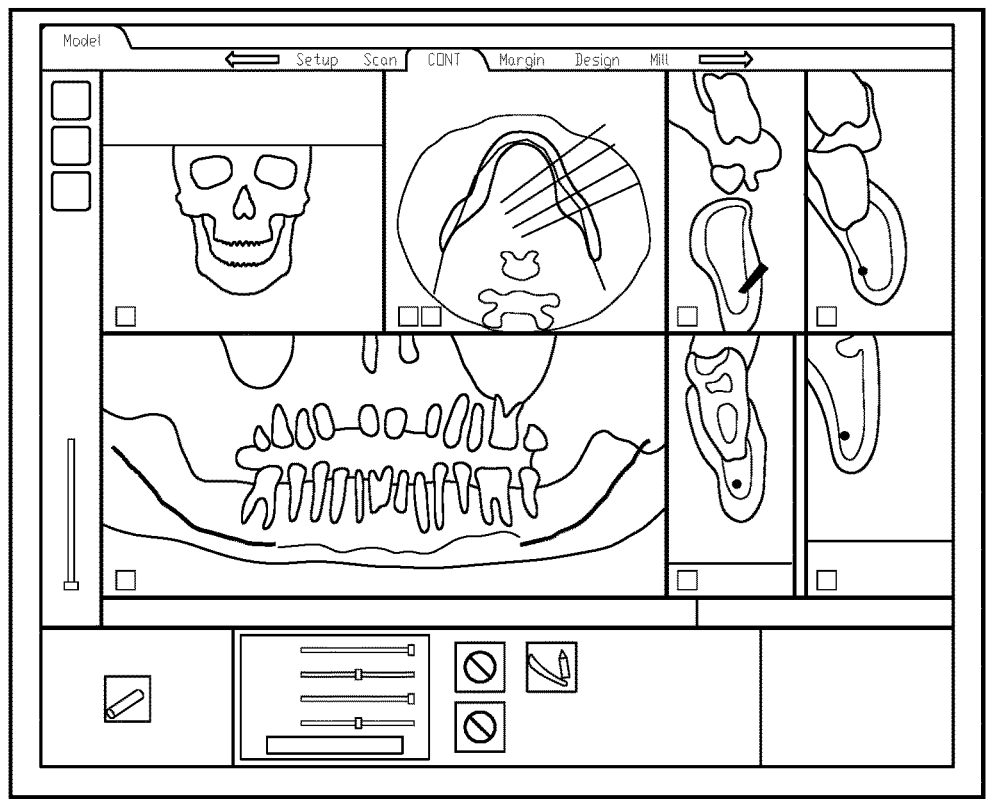
FIG. 1 illustrates an interface displaying 3D cone beam data.

As noted above, this disclosure provides a display method, preferably implemented in a computer, such as a workstation. For illustrated purposes, the workstation is a single machine, but this is not a limitation. More generally, the method is implemented using one or more computing-related entities (systems, machines, processes, programs, libraries, functions, code, or the like) that facilitate or provide the inventive functionality. A representative machine is a computer running commodity hardware, an operating system, an application runtime environment, and a set of applications or processes (e.g., linkable libraries, native code, or the like, depending on platform), that provide the functionality of a given system or subsystem. The invention may be implemented in a standalone machine, or across a distributed set of machines.

In a representative embodiment, a computer workstation in which the invention is implemented comprises hardware, suitable storage and memory for storing an operating system, one or more software applications and data, conventional input and output devices (a display, a keyboard, a point-and-click device, and the like), other devices to provide network connectivity, and the like. An intra-oral digitizer wand is associated with the workstation to obtain optical scans from a patient's anatomy. The digitizer scans the restoration site with a scanning laser system and delivers live images to a monitor on the workstation. An intra-oral digital (IOD) scanner and associated computer-aided design system that may be used for this purpose is the E4D Dentist™ system, manufactured by D4D Technologies, LLC. The E4D Dentist system is a comprehensive chairside CAD CAM system that produces inlays, onlays, full crowns and veneers. A handheld laser scanner in the system captures a true 3-D image either intraorally, from impressions or from models. Design software (e.g., DentaLogic™) in this system is used to create a 3-D virtual model.

Generalizing, a display interface according to this disclosure is generated in software (e.g., a set of computer program instructions) executable in at least one processor. A representative implementation is computer program product comprising a tangible medium on which given computer code is written, stored or otherwise embedded. The display interface comprises an ordered set of display tabs and associated display panels or "viewports." Although the illustrative embodiment shows data sets displayed within multiple viewports on a single display, this is not a limitation, as the various views may be displayed using multiple windows, views, viewports, and the like. The display interface may be web-based, in which case the views of displayed as markup-language pages. The interface exposes conventional display objects such as tabbed views, pull-down menus, browse objects, and the like.

The system also receives cone beam data for a cone beam data source. As noted above, representative commercial systems that implement cone beam scanning are the i-CAT from Imaging Sciences International, Inc. and the GXCB-500 (powered by i-CAT) from Gendex Dental Systems, Inc. These are merely representative, as any convenient source of cone beam data may be used. Moreover, while cone beam data is preferred as the source of the 3D scan, this is not a limitation, as any 3D data source may be used.

Figure 2:
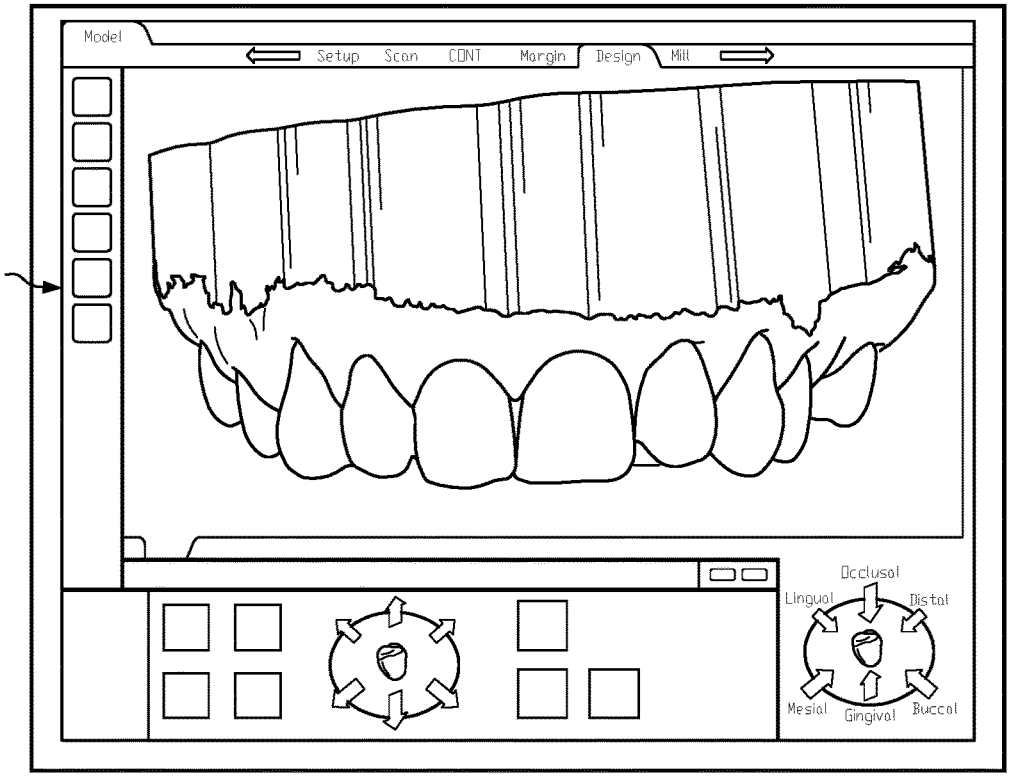
FIG. 2 illustrates an interface displaying a 2D surface model generated by an intra-oral scan.
Figure 3:
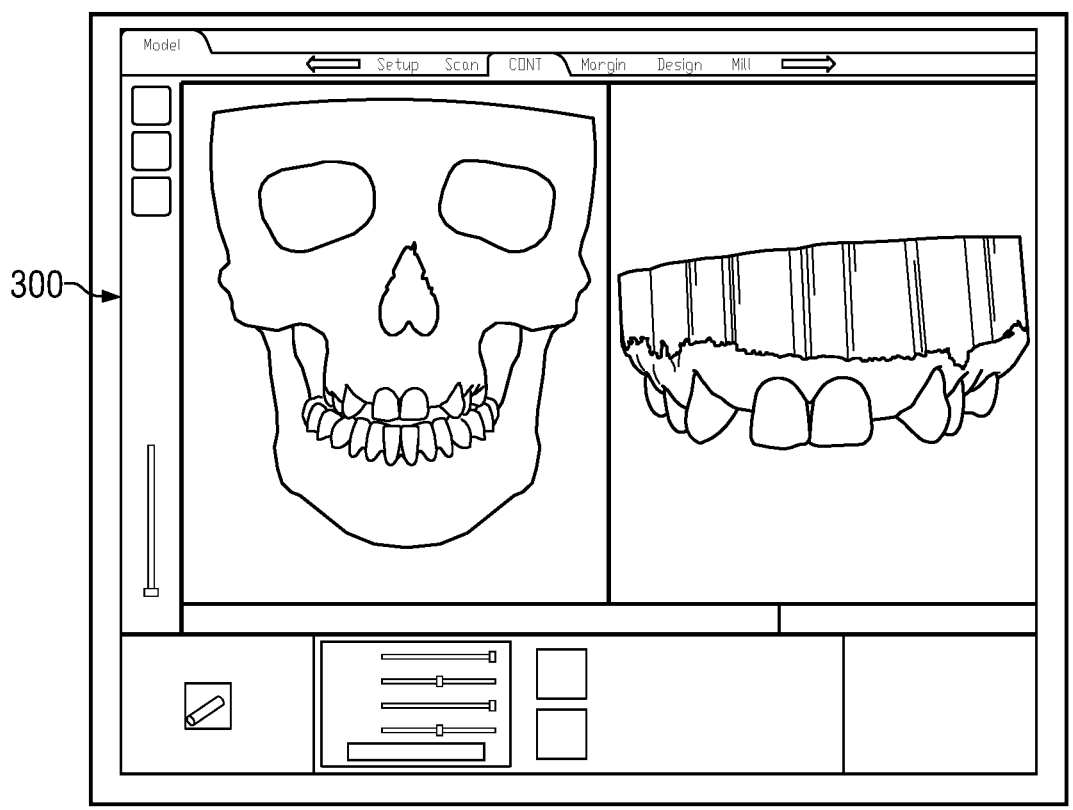
FIG. 3 illustrates an interface showing a pairing of the 3D and 2D scans.

FIG. 1 illustrates several views of a 3D cone beam data displayed on an interface 101, whereas FIG. 2 represents the display interface 201 for the 2D scanned surface map data. In this embodiment, FIG. 2 illustrates the known user interface from the E4D Dentist system available from D4D Technologies, LLC and described by commonly-owned, U.S. Pat. No. 7,184,150, the disclosure of which is incorporated by reference. As is well-known, using that system the prepared area and adjacent teeth are scanned using the digitizer, and a 3D model of the prepared area is obtained. This information is then used to produce a 3D model of a desired restoration. Such a process can be performed using the Design Center available as part of the E4D Dentist system. FIG. 3 illustrates how the 3D and 2D data sets are paired, preferably in a single side-by-side view 300 (although any other convenient orientation may be implemented). In this dual view, the operator simply selects and clicks on what he or she considers are common points on the cone beam data and the scanned data. Typically, three (3) common points on each data set are sufficient to automatically align the data sets. The algorithms and techniques for performing the data set alignment are not part of this disclosure, as there are known techniques and technologies that are useful for this purpose. Any alignment method may be used.

For example, standard methods to align 2D and 3D may include extracting a set of edge points from the 3D data, based in part on characteristics of the 3D data, and computing a transformation that minimizes a cost function based on the sum of the distances between the closest points in the transformed data sets. The computation of the optimal transformation may be iterated until convergence is achieved. An alternative approach may include identifying corresponding feature sets on both 2D and 3D data sets, and computing a transformation that minimizes a cost function based on the sum of distances between the corresponding points. Corresponding feature sets may include regions of high curvature, or specific shapes or structures present in both 2D and 3D data sets.

Figure 4:
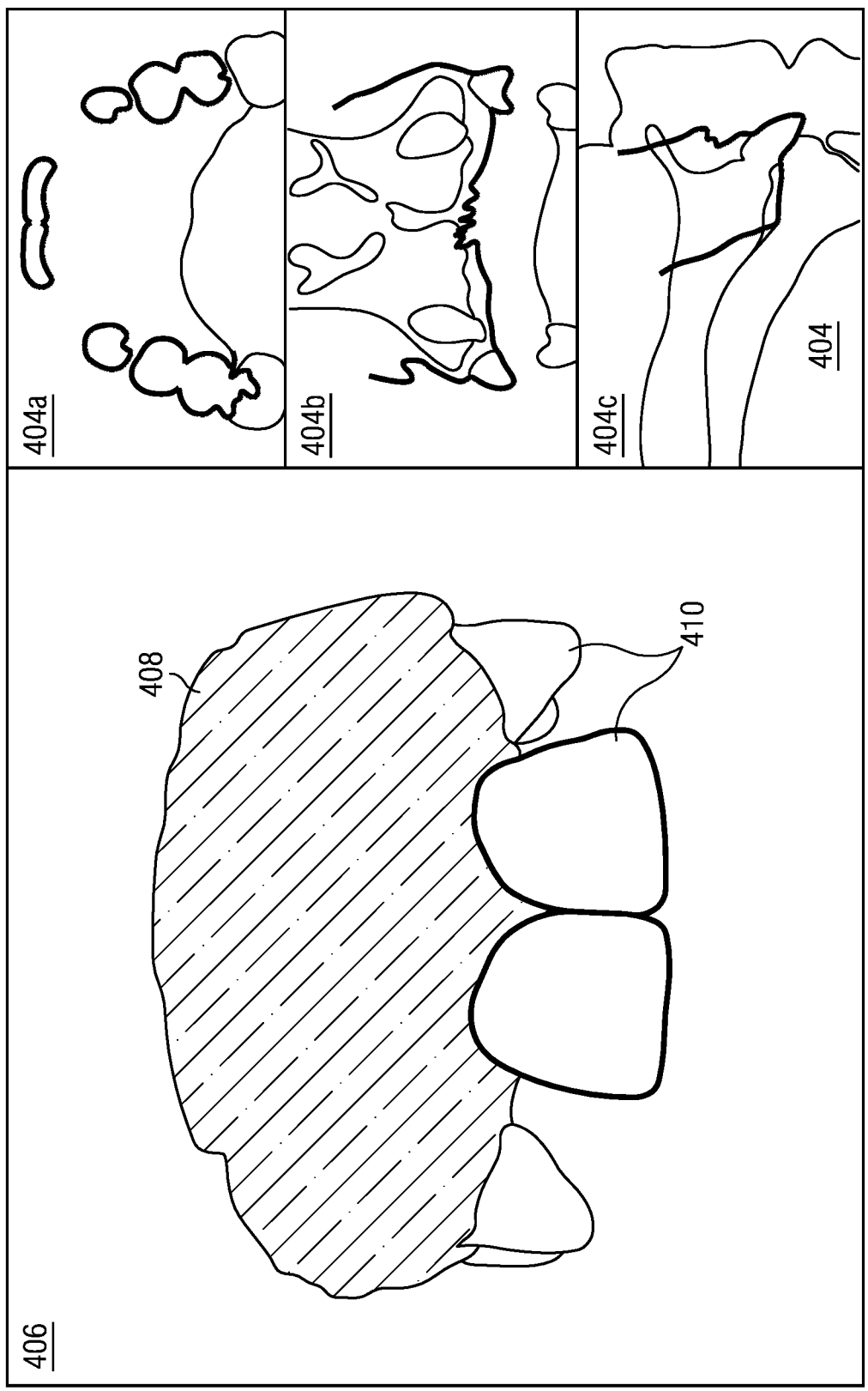
FIG. 4 illustrates an interface according to this invention.

FIG. 4 illustrates the unique display method according to this disclosure. It is assumed that the data sets have been aligned in the manner described above. In a representative embodiment, a display interface 400 includes one or more display areas that enable the operator to visualize and correct alignment errors between the paired 2D and 3D data sets. A display area 404 renders one or more (and preferably three (3) mutually orthogonal views) slices of the cone beam data. Thus, there is a first display slice 404*a*, a second display slice 404*b*, and a third display slice 404*c*. While all three views are not required, they are preferred. A main display area 406 displays a view of a 2D scanned surface map (obtained from an intra-oral scan, or the scan of a model). According to a first aspect, the view of the 2D scanned surface map in the third display area is "textured" by coloring the 2D surface model based on the intensity of each 3D pixel (or "voxel") that it intersects. In view 406, the intensities of the cone beam computed tomography data are overlaid onto the 2D surface of the (in this case) intra-oral scan. In this example, the soft tissue 408 is colored with a lower intensity as compared to the teeth structures 410, and this is because the soft tissue has a lower density than that of the teeth. Thus, the textured view provides the operator with a unique perspective to conform alignment using the visualized hard and soft tissue landmarks. In addition, and according to a second aspect, each of the preferably mutually orthogonal cone view data slices (in viewports 404a-c) is overlaid with a wireframe projection or model from the 2D surface model data. The wireframe projection is shown in the darker (or bold) lines in each of the separate viewports. Preferably, the operator can rotate and move the 2D surface model in any view by clicking and dragging with a data entry device (a mouse or keyboard). The visualizations update, preferably in real-time, as one data set is transformed with respect to the other.

Although not shown in FIG. 4, the display interface may also include a display area for the 3D cone beam data.

Although it is preferred to display the lower density structures with colors of lower intensity, this is not a limitation, as the opposite approach may be used (i.e. displaying lower density structures with colors of higher intensity). Also, in lieu of using color variations, other display constructs (such as shading, symbols, text, numbers, etc.) may be used to illustrate the "texturing."

As used herein, the phrase "display area" should be broadly construed to refer to a window, a sub-window, a display tab, a portion of a display area, a viewport, and the like.

Thus, preferably the textured view is formed by coloring (or shading, or otherwise providing a visual indication on) the surface of the 2D data as a function of the intensity of the spatial points (voxels) at which it intersects the 3D data set. In addition, preferably each slice of the 3D data set (and preferably there are three such mutually orthogonal slices) is superposed with a wireframe projection onto that same slice of the aligned 2D data set. This user interface allows the operator to easily identify and correct any alignment errors, as the interface enables the operator to rigidly transform either data set with respect to the other data set, wherein the underlying alignment routine update and adjust the visualizations accordingly. When the alignment is accurate, the contrast at the gum line of the teeth in the 2D scan is high, because teeth and soft tissue exhibit different intensities in the cone beam data. If the alignment is poor, the change in contrast occurs away from the gum line, making errors in alignment easy to detect and correct. In particular, the operator can use conventional display interface tools to manually manipulate the alignment, e.g., by selecting one of the slice views and dragging the associated wireframe projection to rotate and translate the associated alignment matrix, which updates automatically.

Although not meant to be limiting, the technique described above may be implemented within a dental implant planning software package and system.

Figure 5:
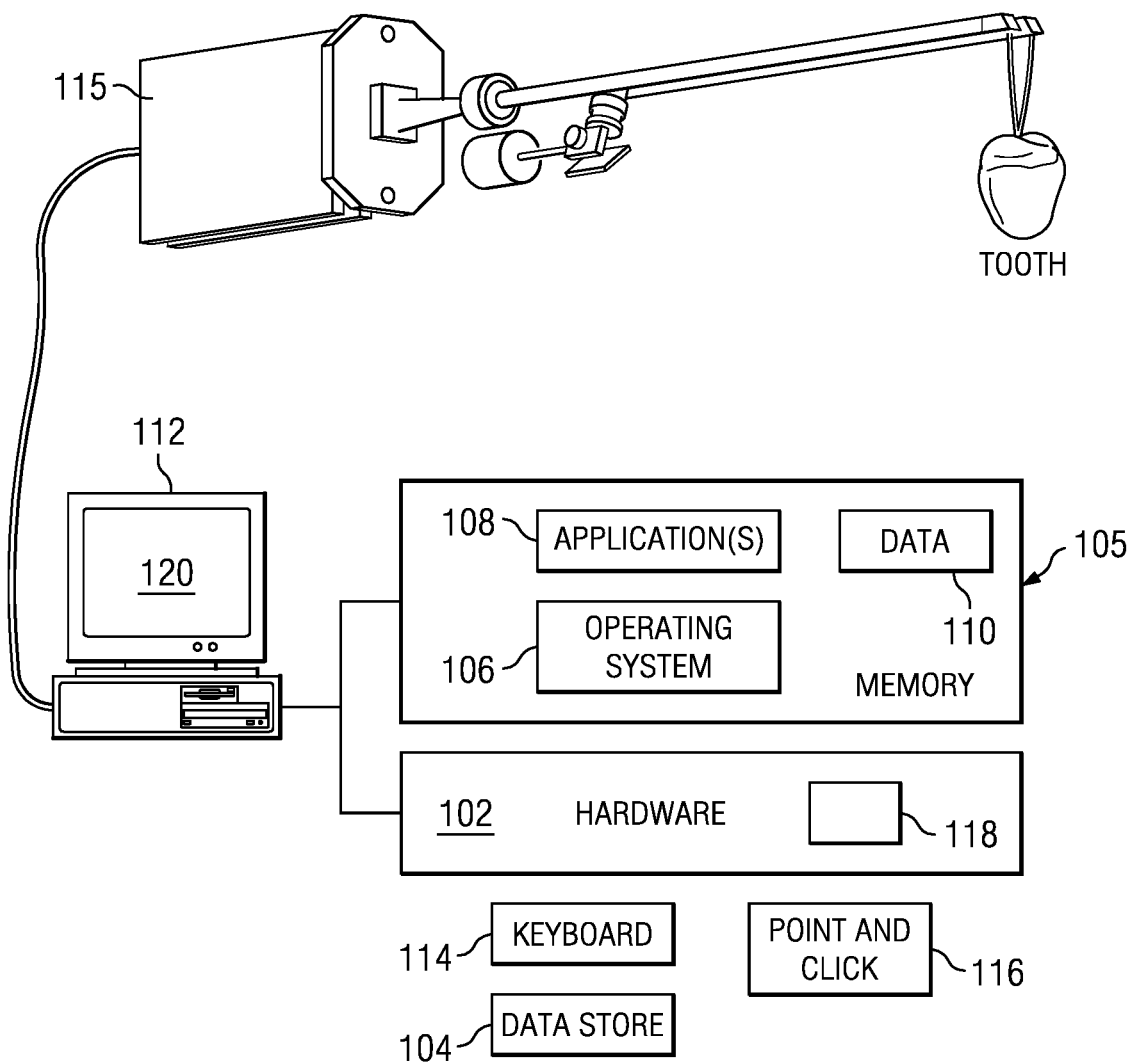
FIG. 5 illustrates a computer system in which the method described herein may be implemented.

Several of the processing steps are performed in a computer. As seen in FIG. 5, a representative computer 100 comprises hardware 102, suitable storage 104 and memory 105 for storing an operating system 106, one or more software applications 108 and data 110, conventional input and output devices (a display 112, a keyboard 114, a point-and-click device 116, and the like), other devices 118 to provide network connectivity, and the like. A laser digitizer system 115 is used to obtain optical scans from a patient's dental anatomy. Using a conventional graphical user interface 120, an operator can view and manipulate scanned information and models as they are rendered on the display 112.

While the above describes a particular order of operations performed by certain embodiments of the invention, it should be understood that such order is exemplary, as alternative embodiments may perform the operations in a different order, combine certain operations, overlap certain operations, or the like. References in the specification to a given embodiment indicate that the embodiment described may include a particular feature, structure, or characteristic, but every embodiment may not necessarily include the particular feature, structure, or characteristic. Further, while given components of the system have been described separately, one of ordinary skill will appreciate that some of the functions may be combined or shared in given systems, machines, devices, processes, instructions, program sequences, code portions, and the like.

Having described our invention, what we claim is as follows.

The invention claimed is:

1. A method of visualizing and correcting alignment errors between 2D and 3D data sets in an implant planning tool, wherein the 3D data set comprises one or more spatial points each having an intensity, comprising:

displaying a textured view that is generated by providing a given display indication on a surface of the 2D data set as a function of intensities of one or more spatial points of the 3D data set at which the surface intersects the 3D data set, where the textured view is generated in software executing in a hardware element responsive to receipt of operator-entered data indicating one or more common points on the 2D data set and the 3D data set and illustrates an alignment between the 2D and 3D data sets;

in association with the textured view, displaying one or more slices of the 3D data set, wherein each of the slices of the 3D data set is overlaid with a wireframe projection from the 2D data set to form a visualization; and responsive to receipt of operator-entered data indicating a rotation or movement of the 2D data set, updating the visualizations as the 2D and 3D data sets are transformed relative to each other.

2. The method as described in claim 1 wherein the 2D data set is a surface map generated from a surface scan, and wherein the 3D data set is volume data generated from a cone beam scan.

3. The method as described in claim 1 wherein the given display indication is a coloration.

4. The method as described in claim 1 wherein the slices of the 3D set are mutually-orthogonal, and wherein each slice is displayed in a dedicated display area.

5. An apparatus for use in visualizing and correcting alignment errors between 2D and 3D data sets in an implant planning tool, wherein a 3D data set comprises one or more spatial points each having an intensity, comprising:

a processor;

computer memory storing computer program instructions executed by the processor to perform operations comprising:

displaying a textured view that is generated by providing a given display indication on a surface of the 2D data set as a function of intensities of one or more spatial points of the 3D data set at which the surface intersects the 3D data set, where the textured view is generated in response to receipt of operator-entered data indicating one or more common points on the 2D data set and the 3D data set and illustrates an alignment between the 2D and 3D data sets;

in association with the textured view, displaying one or more slices of the 3D data set, wherein each of the slices of the 3D data set is overlaid with a wireframe projection from the 2D data set to form a visualization; and responsive to receipt of operator-entered data indicating a rotation or movement of the 2D data set, updating the visualizations as the 2D and 3D data sets are transformed relative to each other.

6. The apparatus as described in claim 5 wherein the 2D data set is a surface map generated from a surface scan, and wherein the 3D data set is volume data generated from a cone beam scan.

7. The apparatus as described in claim 5 wherein the given display indication is a coloration.

8. The apparatus as described in claim 5 wherein the slices of the 3D data set are mutually-orthogonal, and wherein each slice is displayed in a dedicated display area.

9. An article comprising a non-transitory tangible machine-readable medium that stores a program, wherein a 3D data set comprises one or more spatial points each having an intensity, the program being executed by a machine to perform operations comprising:

displaying, on a display device associated with the machine, a textured view that is generated by providing a given display indication on a surface of a 2D data set as a function of intensities of one or more spatial points of the 3D data set at which the surface intersects a 3D data set, where the textured view is generated in response to receipt of operator-entered data indicating one or more common points on the 2D data set and the 3D data set and illustrates an alignment between the 2D and 3D data sets;

in association with the textured view, displaying one or more slices of the 3D data set, wherein each of the slices of the 3D data set is overlaid with a wireframe projection from the 2D data set to form a visualization; and responsive to receipt of operator-entered data indicating a rotation or movement of the 2D data set, updating the visualizations as the 2D and 3D data sets are transformed relative to each other.

10. The article as described in claim 9 wherein the 2D data set is a surface map generated from a surface scan, and wherein the 3D data set is volume data generated from a cone beam scan.

11. The article as described in claim 9 wherein the given display indication is a coloration.

12. The article as described in claim 9 wherein the slices of the 3D data set are mutually-orthogonal, and wherein each slice is displayed in a dedicated display area.

* * * * *